(12) United States Patent  
Neumann et al.

(10) Patent No.: US 9,272,979 B2  
(45) Date of Patent: Mar. 1, 2016

(54) PROCESS FOR SEPARATING VINYL ESTERS FROM A GAS STREAM COMPRISING ETHYLENE AND VINYL ESTERS

(71) Applicant: Basell Polyolefine GmbH, Wesseling (DE)

(72) Inventors: Erich Neumann, Braunschweig (DE); Christoph Wolf, Pulheim-Dansweiler (DE); Dieter Littmann, Mücke (DE)

(73) Assignee: Basell Polyolefine GmbH, Wesseling (DE)

( * ) Notice: Subject to any disclaimer, the term of this patent is extended or adjusted under 35 U.S.C. 154(b) by 0 days.

(21) Appl. No.: 14/654,100

(22) PCT Filed: Dec. 16, 2013

(86) PCT No.: PCT/EP2013/076680  
§ 371 (c)(1),  
(2) Date: Jun. 19, 2015

(87) PCT Pub. No.: WO2014/095707  
PCT Pub. Date: Jun. 26, 2014

(65) Prior Publication Data  
US 2015/0315119 A1     Nov. 5, 2015

(30) Foreign Application Priority Data  
Dec. 20, 2012   (EP) .................................... 12198347

(51) Int. Cl.  
*C08F 2/00*     (2006.01)  
*C08F 4/00*     (2006.01)  
(Continued)

(52) U.S. Cl.  
CPC ............... *C07C 67/52* (2013.01); *C08F 210/02* (2013.01)

(58) Field of Classification Search  
CPC ....... C07C 67/52; C07C 69/15; C08F 210/02; C08F 2/00; C08F 218/08  
USPC ............................... 526/64, 89, 319; 560/248  
See application file for complete search history.

(56) References Cited

U.S. PATENT DOCUMENTS

| 4,260,722 A | 4/1981 | Pfleger et al. |
| 6,300,430 B1 | 10/2001 | Deckers et al. |

(Continued)

FOREIGN PATENT DOCUMENTS

| WO | WO 99/14251 A1 | 3/1999 |
| WO | WO 2008/019873 A1 | 2/2008 |

(Continued)

OTHER PUBLICATIONS

PCT International Search Report & Written Opinion mailed Feb. 4, 2014, for PCT/EP2013/076680.

*Primary Examiner* — William Cheung

(57) ABSTRACT

A process for separating esters of vinyl alcohol from a gas stream comprising from 70 to 99.5% by weight of ethylene and from 0.5 to 30% by weight of esters of vinyl alcohol being at a pressure in the range of from 0.5 MPa to 10 MPa and a temperature in the range of from 5° C. to 50° C.; and a process for copolymerizing ethylene and esters of vinyl alcohol in the presence of free-radical polymerization initiators at pressures in the range of from 110 MPa to 500 MPa and temperatures in the range of from 100° C. to 350° C. in a continuously operated polymerization apparatus comprising such a process for separating esters of vinyl alcohol from a gas stream comprising from 70 to 99.5% by weight of ethylene and from 0.5 to 30% by weight of esters of vinyl alcohol.

12 Claims, 2 Drawing Sheets

(51) Int. Cl.
*C08F 118/02* (2006.01)
*C07C 67/48* (2006.01)
*C07C 67/52* (2006.01)
*C08F 210/02* (2006.01)

(56) References Cited

U.S. PATENT DOCUMENTS

2005/0037219 A1 2/2005 Ohlsson et al.
2012/0136170 A1* 5/2012 Rinne .................. C07C 67/055
560/248
2013/0085241 A1 4/2013 Solis et al.
2013/0274424 A1 10/2013 Weiand et al.

FOREIGN PATENT DOCUMENTS

WO WO2012/084771 A1 * 6/2012
WO WO 2012/084772 A1 6/2012
WO WO 2013/052264 A1 4/2013

* cited by examiner

PROCESS FOR SEPARATING VINYL ESTERS FROM A GAS STREAM COMPRISING ETHYLENE AND VINYL ESTERS

This application is the U.S. National Phase of PCT International Application PCT/EP2013/076680, filed Dec. 16, 2013, claiming benefit of priority to European Patent Application No. 12198347.2, filed Dec. 20, 2012, the content of which is incorporated herein by reference in its entirety.

FIELD OF THE INVENTION

The present invention relates to a process for separating esters of vinyl alcohol from a gas stream comprising from 70 to 99.5% by weight of ethylene and from 0.5 to 30% by weight of esters of vinyl alcohol being at a pressure in the range of from 0.5 MPa to 10 MPa and a temperature in the range of from 5° C. to 50° C. The present invention further relates to a process for copolymerizing ethylene and esters of vinyl alcohol in the presence of free-radical polymerization initiators at pressures in the range of from 110 MPa to 500 MPa and temperatures in the range of from 100° C. to 350° C. in a continuously operated polymerization apparatus comprising such a process for separating esters of vinyl alcohol from a gas stream comprising from 70 to 99.5% by weight of ethylene and from 0.5 to 30% by weight of esters of vinyl alcohol.

BACKGROUND OF THE INVENTION

Polyethylene is the most widely used commercial polymer. It can be prepared by a couple of different processes. Polymerization in the presence of free-radical initiators at elevated pressures was the method first discovered to obtain polyethylene and continues to be a valued process with high commercial relevance for the preparation of low density polyethylene (LDPE).

A normal set-up of a plant for polymerizing or copolymerizing ethylenically unsaturated monomers such as ethylene and esters of vinyl alcohol in the presence of free-radical polymerization initiators consists essentially of a set of two compressors, a low-pressure and a high-pressure compressor, a polymerization reactor, which can be an autoclave or a tubular reactor or a combination of such reactors, and two separators for separating the monomer-polymer mixture leaving the reactor, wherein in the first separator, the high-pressure separator, the ethylene and comonomers separated from the monomer-polymer mixture are recycled to the reaction mixture between the low-pressure compressor and the high-pressure compressor, and the ethylene and comonomers separated from the mixture in the second separator, the low-pressure separator, are fed to the low-pressure compressor where it is compressed to the pressure of the fresh ethylene feed, combined with the fresh ethylene feed and the combined streams are further pressurized to the pressure of the high-pressure gas recycle stream. Such a high-pressure polymerization unit normally further includes apparatuses like extruders and granulators for pelletizing the obtained polymer. In case of tubular reactors, monomer supply to the reactor can either be carried out solely in the beginning of the reactor or only partly in the beginning with the other part fed via one or more side feed entries. Moreover, it is also common to introduce initiator in more than one place down the tube, thus creating more than one reaction zone.

Radically initiated high-pressure polymerization is an appropriated method for producing copolymers of ethylene and esters of vinyl alcohol, especially for preparing copolymers of ethylene and esters of vinyl alcohol having a vinyl ester content in the range of from 1% of weight to 45% of weight. Suitable reactors can be stirred autoclave reactors or tubular reactors. Such high-pressure polymerizations are for example described in U.S. Pat. No. 4,091,200 and WO 99/014251 A1.

A common feature for continuously operated polymerization processes, in which non-polymerized monomers are recycled to the polymerization process, is that continuously small amounts of the reaction mixture are discarded or purged from the process to avoid that impurities or inert materials, which are introduced with the raw materials or which form during the polymerization, accumulate in the process. Regarding processes for radically polymerizing ethylene and vinyl esters, EP 012 368 A1 for example describes a process in which gas, mainly ethylene, is taken from the high-pressure recycle stream, passed through a low temperature separator and discharged as off-gas. To be able to operate the polymerization process economically, there is of course the desired to minimize the amount of discarded material and to find ways for reutilizing the discarded materials meaningfully.

In homopolymerizing ethylene in high-pressure processes, it is common practice, if locally possible, to transfer the purged reaction gas back to an ethylene producing or converting unit such as a steam cracker for reprocessing. However, if the purged reaction gas contains higher amounts of comonomers such as esters of vinyl alcohol, it can be that the raw gas washers in the cracker are no longer able to fully remove these comonomers and they pass into the organic phase, in which they are not only impurities but also may degrade into products such as acidic acid which have a high corrosiveness.

Thus, it was the object of the present invention to overcome the disadvantages of the prior art and to provide a process which efficiently and economically separates esters of vinyl alcohol from a gas streams comprising ethylene and esters of vinyl alcohol and allows to transfer the off-gas stream from ethylene-vinyl ester polymerizations with no or only a minor content of esters of vinyl alcohol to an ethylene producing or converting unit and to take the off-gas from the high-pressure polymerization plant at a position of relatively low pressure.

SUMMARY OF THE INVENTION

We found that this object is achieved by a process for separating esters of vinyl alcohol from a gas stream comprising from 70 to 99.5% by weight of ethylene and from 0.5 to 30% by weight of esters of vinyl alcohol being at a pressure in the range of from 0.5 MPa to 10 MPa and a temperature in the range of from 5° C. to 50° C. comprising the steps of
a) cooling the gas stream in a first heat exchanger by means of a cooling medium to a temperature of from −5° C. to 40° C.;
b) withdrawing the not condensed part of the gas stream from the first heat exchanger and transferring it to a second heat exchanger;
c) cooling the gas stream in the second heat exchanger to a temperature of from −20° C. to 5° C.;
d) withdrawing the not condensed part of the gas stream from the second heat exchanger, reducing the pressure of the gas stream to from 0.5 MPa to 3 MPa and transferring it to a separation vessel;
e) withdrawing the not condensed part of the gas stream from the separation vessel and transferring it as cooling medium to the second heat exchanger; and
f) withdrawing the cooling medium as ethylene gas stream with a reduced content of esters of vinyl alcohol from the second heat exchanger.

Furthermore, we have found a process for copolymerizing ethylene and esters of vinyl alcohol in the presence of free-radical polymerization initiators at pressures in the range of from 110 MPa to 500 MPa and temperatures in the range of from 100° C. to 350° C. in a continuously operated polymerization apparatus comprising such a process for separating esters of vinyl alcohol from a gas stream comprising from 70 to 99.5% by weight of ethylene and from 0.5 to 30% by weight of esters of vinyl alcohol.

BRIEF DESCRIPTION OF THE DRAWINGS

The features and advantages of the present invention can be better understood via the following description and the accompanying drawings where.

DETAILED DESCRIPTION OF THE INVENTION

Figure 1:
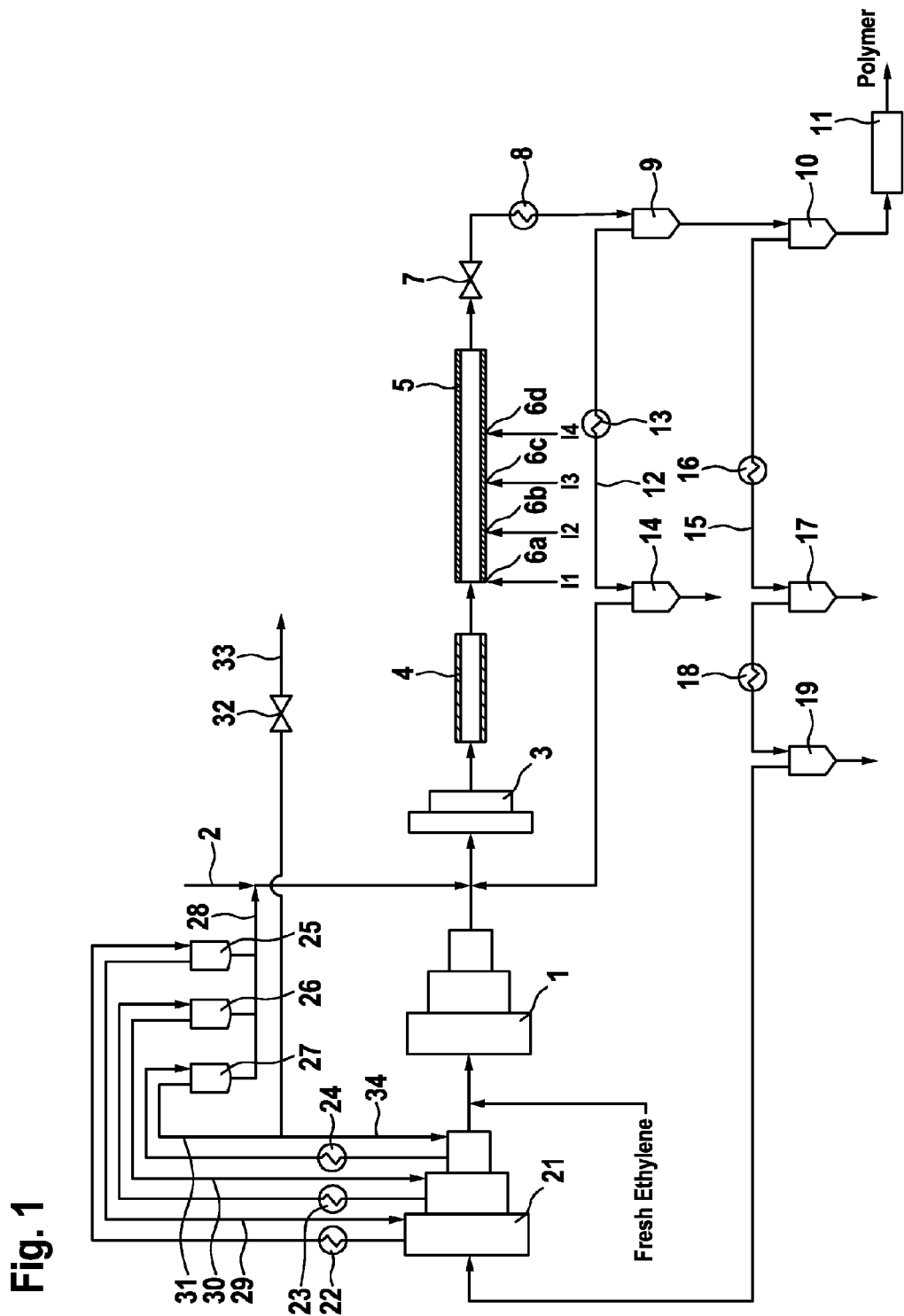
FIG. 1 shows schematically a set-up for a polymerization apparatus with a tubular reactor for copolymerizing ethylene and esters of vinyl alcohol such as vinyl acetate from which a gas stream comprising ethylene and vinyl esters can be taken for separating the stream according to the present invention.

The process of the invention refers to separating esters of vinyl alcohol from a gas stream comprising from 70 to 99.5% by weight of ethylene and from 0.5 to 30% by weight of esters of vinyl alcohol, preferably comprising from 85 to 99% by weight of ethylene and from 1 to 15% by weight of esters of vinyl alcohol and more preferably comprising from 90 to 97% by weight of ethylene and from 3 to 10% by weight of esters of vinyl alcohol. According to the present invention, the pressure of the gas stream is in the range of from 0.5 MPa to 10 MPa, preferably from 1 MPa to 5 MPa and more preferably from 2 MPa to 4 MPa and the temperature is in the range of from 5° C. to 50° C., preferably from 10° C. to 45° C. and more preferably from 15° C. to 40° C.

Preferred esters of vinyl alcohol have a total of from 4 to 15 carbon atoms, such as vinyl acetate, vinyl propionate and vinyl butyrate. An especially preferred vinyl ester is vinyl acetate. In such a case, vinyl acetate is separated from a stream comprising from 70 to 99.5% by weight of ethylene and from 0.5 to 30% by weight of vinyl acetate. It is also possible to separate off mixtures of more than one ester of vinyl alcohol.

The gas stream, from which the ester of vinyl alcohol is separated off, can comprise minor amounts of further components. Usually the amount of these further components is in the range of from 0.1 to 3% by weight. Example of such further components of the gas stream are saturated and unsaturated hydrocarbons having from 1 to 16 carbon atoms such as methane, ethane or propane, propene or 1-butene; aliphatic ketones or aldehydes such as acetaldehyde, propionaldehyde or acetone; or alcohols such as methanol or tert-butanol.

According to the present invention, as step a) of the process for separating esters of vinyl alcohol, the gas stream is cooled by means of a cooling medium in a first heat exchanger to a temperature of from −5° C. to 40° C., preferably from 0° C. to 25° C. and more preferably from 5° C. to 10° C. Suitable cooling media can be any conventional fluids appropriate for being operated in a temperature range of from −20° C. to 50° C. Preferably the cooling medium is a water/glycol mixture.

By cooling the gas stream, a part of the stream condenses and forms a liquid, which is withdrawn from the bottom of the heat exchanger.

In step b) of the process of the present invention, the not condensed part of the gas stream is withdrawn from the first heat exchanger and transferred to a second heat exchanger. Preferably the transfer is carried out by a pressure gradient.

Subsequently, as step c), the gas stream is cooled in the second heat exchanger to a temperature of from −20° C. to 5° C., preferably from −15° C. to 0° C. and more preferably from −12° C. to −5° C. By cooling the gas stream, a part of the stream condenses and forms a liquid, which is withdrawn from the bottom of the heat exchanger.

The not condensed part of the gas stream is thereafter in step d) withdrawn from the second heat exchanger and transferred to a separation vessel, which has a pressure of from 0.2 MPa to 3 MPa, preferably from 0.3 MPa to 1.5 MPa and more preferably from 0.4 MPa to 1 MPa. The pressure reduction is preferably achieved by passing the gas stream through a let-down valve. Caused by the pressure reduction, the temperature of the gas stream decreases, preferably to values of from −70° C. to −10° C., more preferably of from −60° C. to −20° C. and especially of from −50° C. to −30° C. By cooling the gas stream, a part of the stream condenses and forms a liquid, which is withdrawn from the bottom of the heat exchanger.

The part of the gas stream, which is not condensed in the separation vessel, is then in step e) withdrawn from the separation vessel and transferred as cooling medium to the second heat exchanger where it is used as cooling medium for cooling the gas stream coming from the first heat exchanger. The cooling medium withdrawn from the second heat exchanger is an ethylene gas stream with a reduced content of esters of vinyl alcohol with respect to the initial gas mixture. The content of esters of vinyl alcohol in the ethylene gas stream used as cooling medium in the second heat exchanger is usually from 0.005 to 0.5% by weight, preferably from 0.01 to 0.2% by weight and especially from 0.02 to 0.1% by weight.

Preferably, in a subsequently step g), the gas stream coming from the second heat exchanger after having acted as cooling medium is further heated in a third heat exchanger to a temperature of from 10° C. to 50° C., more preferably from 20° C. to 45° C. and especially from 30° C. to 40° C.

The ethylene gas stream with the reduced content of esters of vinyl alcohol can then be reprocessed in all common ways. Preferably this ethylene gas stream is transferred to an ethylene recovery unit or an ethylene producing or converting unit such as a steam cracker for further treatment.

The condensed parts of the gas stream, which are obtained in steps a), c) and d) of the process of the present invention and which mainly consist of esters of vinyl alcohol, are preferably combined and reused. In case that the gas stream comes from a copolymerization process, these liquids are preferably returned to the polymerization process.

By carrying out the separation of esters of vinyl alcohol from a gas stream comprising from 70 to 99.5% by weight of ethylene and from 0.5 to 30% by weight of esters of vinyl alcohol being at a pressure in the range of from 1 MPa to 5 MPa and a temperature in the range of from 10° C. to 50° C. according the process of the present invention it is possible to have the vinyl esters removed from the ethylene by benefitting from the pressure difference between the starting gas mixture and the final purified ethylene stream without requiring a higher amount of external cooling. Furthermore, a high flexibility regarding the quantity of the gas to be treated is achieved since a substantial part of the cooling is self-cooling.

The process for separating esters of vinyl alcohol from a gas stream comprising from 70 to 99.5% by weight of ethylene and from 0.5 to 30% by weight of esters of vinyl alcohol being at a pressure in the range of from 1 MPa to 5 MPa and a temperature in the range of from 10° C. to 50° C. can very advantageously be utilized as part of a process for copolymerizing ethylene and esters of vinyl alcohol, especially for purifying such gas mixtures which are off-gas from a continuously operated polymerization apparatus.

Accordingly the present invention also refers to process for copolymerizing ethylene and esters of vinyl alcohol in the presence of free-radical polymerization initiators at pressures in the range of from 110 MPa to 500 MPa and temperatures in the range of from 100° C. to 350° C. in a continuously operated polymerization apparatus comprising such a processes for separating esters of vinyl alcohol from a gas stream comprising from 70 to 99.5% by weight of ethylene and from 0.5 to 30% by weight of esters of vinyl alcohol.

In the process for copolymerizing ethylene and esters of vinyl alcohol, it is possible to use additional comonomers beside ethylene and vinyl esters. Examples of suitable additional comonomers are α,β-unsaturated $C_3$-$C_8$-carboxylic acids, in particular maleic acid, fumaric acid, itaconic acid, acrylic acid, methacrylic acid and crotonic acid, derivatives of α,β-unsaturated $C_3$-$C_8$-carboxylic acids, e.g. unsaturated $C_3$-$C_{15}$-carboxylic esters, in particular esters of $C_1$-$C_6$-alkanols, or anhydrides, in particular methyl methacrylate, ethyl methacrylate, n-butyl methacrylate or tert-butyl methacrylate, methyl acrylate, ethyl acrylate, n-butyl acrylate, 2-ethylhexyl acrylate, tert-butyl acrylate, methacrylic anhydride, maleic anhydride or itaconic anhydride, and 1-olefins such as propene, 1-butene, 1-pentene, 1-hexene, 1-octene or 1-decene. Propene, 1-butene, 1-hexene, acrylic acid, n-butyl acrylate, tert-butyl acrylate, or 2-ethylhexyl acrylate are particularly suitable as additional comonomer. However, most preferably the copolymerization of the present invention is only a copolymerization of ethylene and esters of vinyl alcohol.

The obtained ethylene copolymers have preferably a comonomer content of from 3 to 50% by weight, more preferably from 5 to 45% by weight and especially of from 10 to 40% by weight, Accordingly, the proportion of comonomer or comonomers in the reaction mixture is preferably from 3 to 50% by weight and more preferably from 5 to 45% by weight, based on the amount of monomers, i.e. the sum of ethylene and all comonomers. Depending on the type of comonomer, it can be preferred to feed the comonomers at a plurality of different points to the reactor.

For the purposes of the present invention, polymers are all substances which are made up of at least two monomer units. They are preferably copolymers having an average molecular weight $M_n$ of more than 20 000 g/mole. However, the method of the invention can also be advantageously employed in the preparation of oligomers, waxes and polymers having a molecular weight $M_n$ of less than 20 000 g/mole.

Possible initiators for starting the free-radical polymerization in the respective reaction zones are in general all substances that can produce radical species under the conditions in the polymerization reactor. Examples for such free-radical polymerization initiators are organic peroxides or azo compounds which both represent a preferred embodiment of the process of the present invention. Examples of suitable organic peroxides are peroxy esters, peroxy ketals, peroxy ketones and peroxycarbonates, e.g. di(2-ethylhexyl) peroxydicarbonate, dicyclohexyl peroxydicarbonate, diacetyl peroxydicarbonate, tert-butyl peroxyisopropylcarbonate, di-tert-butyl peroxide, di-tert-amyl peroxide, dicumyl peroxide, 2,5-dimethyl-2,5-di-tert-butylperoxyhexane, tert-butyl cumyl peroxide, 2,5-dimethyl-2,5-di(tert-butylperoxy)hex-3-yne, 1,3-di-isopropyl monohydroperoxide or tert-butyl hydroperoxide, didecanoyl peroxide, 2,5-dimethyl-2,5-di(2-ethylhexanoylperoxy)hexane, tert-amyl peroxy-2-ethylhexanoate, dibenzoyl peroxide, tert-butyl peroxy-2-ethylhexanoate, tert-butyl peroxydiethylacetate, tert-butyl peroxydiethylisobutyrate, tert-butyl peroxy-3,5,5-trimethylhexanoate, 1,1-di(tert-butylperoxy)-3,3,5-trimethylcyclohexane, 1,1-di(tert-butylperoxy)cyclohexane, tert-butyl peroxyacetate, cumyl peroxyneodecanoate, tert-amyl peroxyneodecanoate, tert-amyl peroxypivalate, tert-butyl peroxyneodecanoate, tert-butyl permaleate, tert-butyl peroxypivalate, tert-butyl peroxyisononanoate, diisopropylbenzene hydroperoxide, cumene hydroperoxide, tert-butyl peroxybenzoate, methyl isobutyl ketone hydroperoxide, 3,6,9-triethyl-3,6,9-trimethyl-triperoxocyclononane and 2,2-di(tert-butylperoxy)butane. Azoalkanes (diazenes), azodicarboxylic esters, azodicarboxylic dinitriles such as azobisisobutyronitrile and hydrocarbons which decompose into free radicals and are also referred as C-C initiators, e.g. 1,2-diphenyl-1,2-dimethylethane derivatives and 1,1,2,2-tetramethylethane derivatives, are also suitable. It is possible to use either individual initiators or preferably mixtures of various initiators. A large range of initiators, in particular peroxides, are commercially available, for example the products of Akzo Nobel offered under the trade names Trigonox® or Perkadox®.

In a preferred embodiment, peroxidic polymerization initiators having a relatively high decomposition temperature are used. Suitable peroxidic polymerization initiators include, for example, di-(2-ethylhexyl)peroxydicarbonate, tert-butyl peroxy-2-ethylhexanoate, 1,1-di(tert-butylperoxy)cyclohexane, 2,2-di(tert-butylperoxy)butane, tert-butyl peroxy-3,5,5-trimethylhexanoate, tert-butyl peroxybenzoate, 2,5-dimethyl-2,5-di(tert-butylperoxy)hexane, tert-butyl cumyl peroxide, di-tert-butyl peroxide and 2,5-dimethyl-2,5-di(tert-butylperoxy)hex-3-yne, and particular preference is given to using tert-butyl peroxy-3,5,5-trimethylhexanoate, di-(2-ethylhexyl)peroxydicarbonate or tert-butyl peroxy-2-ethylhexanoate.

The initiators can be employed individually or as a mixture in concentrations of from 0.1 mol/t to 50 mol/t of ethylene copolymer produced, in particular from 0.2 mol/t to 20 mol/t, in each reaction zone. In a preferred embodiment of the present invention the free-radical polymerization initiator, which is fed to a reaction zone, is a mixture of at least two different azo compounds or organic peroxides. If such initiator mixtures are used it is preferred that these are fed to all reaction zones. There is no limit for the number of different initiators in such a mixture, however preferably the mixtures are composed of from two to six and in particular of two, three or four different initiators. Particular preference is given to using mixtures of initiators which have different decomposition temperatures.

It is often advantageous to use the initiators in the dissolved state. Examples of suitable solvents are ketones and aliphatic hydrocarbons, in particular octane, decane and isododecane and also other saturated $C_8$-$C_{25}$-hydrocarbons. The solutions comprise the initiators or initiator mixtures in proportions of from 2 to 65% by weight, preferably from 5 to 40% by weight and particularly preferably from 10 to 30% by weight.

In the process of the invention, the molecular weight of the copolymers to be prepared can as usual be altered by addition of modifiers which act as chain-transfers agents. Examples of suitable modifiers are hydrogen, aliphatic and olefinic hydrocarbons, e.g. propane, butane, pentane, hexane, cyclohexane, propene, 1-butene, 1-pentene or 1-hexene, ketones such as acetone, methyl ethyl ketone (2-butanone), methyl isobutyl ketone, methyl isoamyl ketone, diethyl ketone or diamyl ketone, aldehydes such as formaldehyde, acetaldehyde or propionaldehyde and saturated aliphatic alcohols such as methanol, ethanol, propanol, isopropanol or butanol. Particular preference is given to using saturated aliphatic aldehydes, in particular propionaldehyde or 1-olefins such as propene, 1-butene or 1-hexene, or aliphatic hydrocarbons such as propane.

The copolymerization of ethylene and esters of vinyl alcohol process is preferably carried out at pressures of from 110 MPa to 500 MPa, with pressures of from 160 MPa to 350 MPa being preferred and pressures of from 200 MPa to 330 MPa being particularly preferred. The temperatures are in the range from 100° C. to 350° C., preferably from 120° C. to 300° C. and very particularly preferably from 130° C. to 290° C.

The process of the present invention can be carried out with all types of high-pressure reactors appropriate for high-pressure polymerization. Suitable high-pressure reactors are, for example, tubular reactors or autoclave reactors or combinations of such reactors. Preferably the high-pressure reactors are tubular reactors or autoclave reactors and in particular tubular reactors. Common high-pressure autoclave reactors are stirred reactors and have a length-to-diameter ratio of in the range from 2 to 30, preferably from 10 to 20. Appropriate tubular reactors are basically long, thick-walled pipes, which are usually from about 0.5 km to 4 km, preferably from 1 km to 3 km and especially from 1.5 km to 2.5 km long. The inner diameter of the pipes is usually in the range of from about 30 mm to 120 mm and preferably from 40 mm to 90 mm. Such tubular reactors have preferably a length-to-diameter ratio of greater than 1000, preferably from 10000 to 40000 and especially from 25000 to 35000.

Preferred tubular reactors have at least two reaction zones, preferably from 2 to 6 reaction zones and more preferably from 2 to 5 reaction zones. The number of reaction zones is given by the number of feeding points for the initiator. Such a feeding point can, for example, be an injection point for a solution of azo compounds or organic peroxides. Fresh initiator is added to the reactor, where it decomposes into free radicals and initiates further polymerization. The generated heat of the reaction rises the temperature of the reaction mixture, since more heat is generated than can be removed through the walls of the tubular reactor. The rising temperature increases the rate of decomposition of the free-radical initiators and accelerates polymerization until essentially all free-radical initiator is consumed. Thereafter no further heat is generated and the temperature decreases again since the temperature of the reactor walls is lower than that of the reaction mixture. Accordingly, the part of the tubular reactor downstream of an initiator feeding point in which the temperature rises is the reaction zone, while the part thereafter, in which the temperature decreases again, is predominantly a cooling zone. The amount and nature of added free-radical initiators determines how much the temperature rises and accordingly allows adjusting that value. Normally, the temperature rise is set to be in the range of from 70° C. to 150° C. in the first reaction zone and 50° C. to 110° C. for the subsequent reaction zones depending on the product specifications and the reactor configuration.

The compression of the monomer mixture to the polymerization pressure is usually carried out by at least two sequentially operating compressors in which a low-pressure compressor first compresses the monomer mixture to a pressure of from 10 MPa to 50 MPa and a high-pressure compressor then further compresses the monomer mixture to the polymerization pressure of from 110 MPa to 500 MPa. Preferably the low-pressure compressor and the high-pressure compressor are multistage compressors. It is further possible to separate one or more stages of one or both of these compressors and divide them into separated compressors. However, usually a series of one low-pressure compressor and one high-pressure compressor is used for compressing the monomer mixture to the polymerization pressure. In such cases, sometimes the whole low-pressure compressor is designated as primary compressor. However, it is also common to designate the one or more first stages of the low-pressure compressor, which compress the recycle gas from the low-pressure separator to the pressure of the fresh ethylene feed, as booster compressor and the one or more further stages as primary compressor although they are all part of one apparatus.

Commonly the polymerization apparatus comprises, beside the polymerization reactor, a high-pressure gas recycle line for recycling gas separated in a high-pressure separator from the reaction mixture and a low-pressure gas recycle line for recycling gas separated in a low-pressure separator from the reaction mixture. The gas recycled in the high-pressure gas recycle line is then fed to the high-pressure compressor and the gas recycled in the low-pressure gas recycle line is fed to the low-pressure compressor, preferably to the foremost of the stages. Preferably, the recycled gas coming from the low-pressure gas recycle line is compressed by the booster compressor to the pressure of the fresh feed of ethylenically unsaturated monomers, preferably ethylene, thereafter combined with the fresh gas feed and the combined gases are further compressed in the primary compressor to the pressure of from 10 MPa to 50 MPa. Preferably, the low-pressure compressor, i.e. the combination of booster compressor and primary compressor, comprises five or six compression stages, two or three in the booster compressor before adding the fresh gas and two or three in the primary compressor after adding the fresh gas.

The compressed monomer mixture is usually cooled after each compression stage of the low-pressure compressor and the fraction of the gas mixture, which is liquid after this cooling, is separated off and returned to the polymerization apparatus in liquid form. Preferably the liquid fractions obtained after the individuals compression stages are first combined before being returned to the polymerization apparatus. Preferably these liquids are recycled to a position between the low-pressure compressor and the high-pressure compressor.

In a preferred embodiment of the present invention, a gas stream comprising from 70 to 99.5% by weight of ethylene and from 0.5 to 30% by weight of esters of vinyl alcohol is taken as off-gas from the continuously operated polymerization apparatus, wherein the off-gas is a part of the compressed monomer mixture after the last compression stage before the fresh ethylene is added and after the liquid fraction obtained in cooling this compressed monomer mixture is separated. By selecting this position for taking the off-gas, only material is purged which has at least once passed the polymerization reactor. However, by having passed at least one previous compression stage in which the compressed monomer mixture is cooled and partly condensed, this position provides the composition of non-reacted monomers, which has the lowest content of vinyl esters. Moreover, this position provides a gas stream which has an appropriated pressure range which is not so high that compressing energy is wasted, however has a sufficiently high pressure that a cooling by expanding the gas can be achieved.

Preferably, at least a part of the liquid fractions obtained after compressing the monomer mixture in the pressure range of from 0.1 MPa to 10 MPa is purified before being returned to the polymerization process. That means, at least a part of the liquid obtained after compressing in stages of the booster compressor are purified. Preferably the whole amount of the liquids is purified.

Preferably the purification of the separated liquid fraction comprises a distillation step, more preferably a two-step distillation. In a preferred embodiment of the present invention, the liquid fraction is fed to a first distillation column, preferably at a position in the center of the column. A relatively high boiling fraction, which usually contains as main components hydrocarbons having eight or more carbon atoms, for example isodocecane which is commonly used as solvent for initiators, acetic acid and tert-butanol, is then withdrawn at the bottom of the column and preferably discarded. A relatively low boiling fraction is withdrawn from the top of the column and transferred to a second distillation column, preferably at a position in the center of the column. A relatively low boiling fraction, which usually contains as main components acetaldehyde, acetone, methanol and traces of water, is withdrawn at the top of the second distillation column and preferably discarded. Purified vinyl esters such as vinyl acetate are then withdrawn from the bottom of second distillation column.

It is also preferred that the purification of the separated liquid fraction comprises a step of water removal by means of a molecular sieve.

In a preferred embodiment of the present invention the liquid fractions are both purified by distillation and by removing water by means of a molecular sieve. Then preferably the liquid fractions are first purified by distillation, preferably a two-step distillation, and thereafter treated by a molecular sieve. In such a set-up, the fresh comonomer feed is then preferably also first send to the water removal unit and thereafter fed to the polymerization apparatus together with the purified liquid coming from the distillation step. In such a case the water content of the fresh comonomer is usually reduced from about 200 to 400 ppm (mass/mass) to less than 30 ppm (mass/mass).

FIG. 1 shows schematically a set-up for a polymerization apparatus with a tubular reactor for copolymerizing ethylene and esters of vinyl alcohol such as vinyl acetate from which a gas stream comprising ethylene and vinyl esters is drawn off which can then be separated according to the present invention. The polymerization process is described on the basis of vinyl acetate as vinyl ester comonomer, however this non-limiting the scope of the invention.

The fresh ethylene, which has a pressure of 4.0 MPa, is added to the polymerization system upstream of a primary compressor (1), by which it is compressed together with recycle gas to a pressure of about 28 MPa. The fresh vinyl acetate is added via line (2). Thereafter the gas mixture is compressed to the polymerization pressure of about 300 MPa using a high-pressure compressor (3). The monomer mixture leaving the high-pressure compressor (3) is fed to pre-heater (4), where the reaction mixture is preheated to the reaction start temperature of from about 120° C. to 180° C., and then conveyed to the tubular reactor (5).

The tubular reactor (5) is basically a long, thick-walled pipe with cooling jackets to remove the liberated heat of reaction from the reaction mixture by means of a coolant circuit (not shown). It is usually from about 0.5 km to 4 km, preferably from 1 km to 3 km and especially from 1.5 km to 2.5 km long. The inner diameter of the pipe is usually in the range of from about 30 mm to 120 mm and preferably from 60 mm to 90 mm.

The tubular reactor (5) shown in FIG. 1 has four spatially separated initiator injection points (6a) to (6d) for feeding initiators or initiator mixtures I1 to I4 to the reactor and accordingly also four reaction zones. By feeding suitable free-radical initiators, which decompose at the temperature of the reaction mixture, to the tubular reactor the polymerization reaction starts. The generated heat of the reaction rises the temperature of the reaction mixture, since more heat is generated than can be removed through the walls of the tubular reactor.

The amount and nature of added free-radical initiators determines how much the temperature rises and accordingly allows adjusting that value. Normally, the temperature rise in the first reaction zone is set to be in the range of from 70° C. to 150° C. and 50° C. to 110° C. for the subsequent reaction zones depending on the product specifications and reactor configuration. The reaction mixture leaves the tubular reactor (5) through a high-pressure let-down valve (7) and passes a post reactor cooler (8). Thereafter, the resulting polymer is separated off from unreacted ethylene and vinyl acetate and from other low molecular weight compounds (oligomers, polymers, additives, solvent, etc.) by means of a high-pressure separator (9) and a low-pressure separator (10), discharged and pelletized via an extruder and granulator (11).

The part of ethylene and vinyl acetate which has been separated off in the high-pressure separator (9) is fed back to the inlet end of the tube reactor (5) in the high-pressure circuit (12) at 28 MPa. It is first freed from other constituents in at least one purification stage and then added to the monomer stream between primary compressor (1) and high-pressure compressor (3). FIG. 1 shows one purification stage consisting of a heat exchanger (13) and a separator (14). It is however also possible to use a plurality of purification stages. The high-pressure circuit (12) usually separates waxes.

The ethylene and the non-reacted vinyl acetate which have been separated off in the low-pressure separator (10) and which further comprise, inter alia, the major part of the low molecular weight products of the polymerization (oligomers), is worked up in the low-pressure circuit (15) at a pressure of from about 0.1 to 0.4 MPa in a plurality of separators with a heat exchanger being located between each of the separators and then fed to a booster compressor (21), in which it is compressed to a pressure of about 4 MPa and then conveyed to primary compressor (1). Booster compressor (21) and primary compressor (1) are preferably part of one low-pressure compressor, i.e. of one apparatus powered by one motor. FIG. 1 shows two purification stages consisting of heat exchangers (16) and (18) and separators (17) and (19). It is however also possible to use only one purification stage or preferably more than two purification stages. The low-pressure circuit (15) usually separates oil and waxes.

The gas mixtures compressed in the individual stages of the booster compressor (21) are cooled after every stage by heat exchanges (22), (23) and (24). Caused by the limited solubility of vinyl acetate in ethylene in the respective pressure range, a part of the vinyl acetate condenses by cooling the gas mixture and is separated off in separators (25), (26) and (27). The liquid phases, mainly consisting of vinyl acetate, are combined and returned to the polymerization process via line (28). It is also possible first to purify the vinyl acetate and thereafter to return it to the polymerization process. The gaseous phases withdrawn from separators (25) and (26) are returned to the corresponding next compression stages via lines (29) and (30).

The gaseous phases comprising ethylene and vinyl acetate withdrawn from separators (27) via line (31) is partly discharged from the polymerization process and transferred via a regulation valve (32) and line (33) to a unit for separating ethylene and vinyl acetate. The remaining part of the gaseous phases is returned to the polymerization process via line (34).

Figure 2:
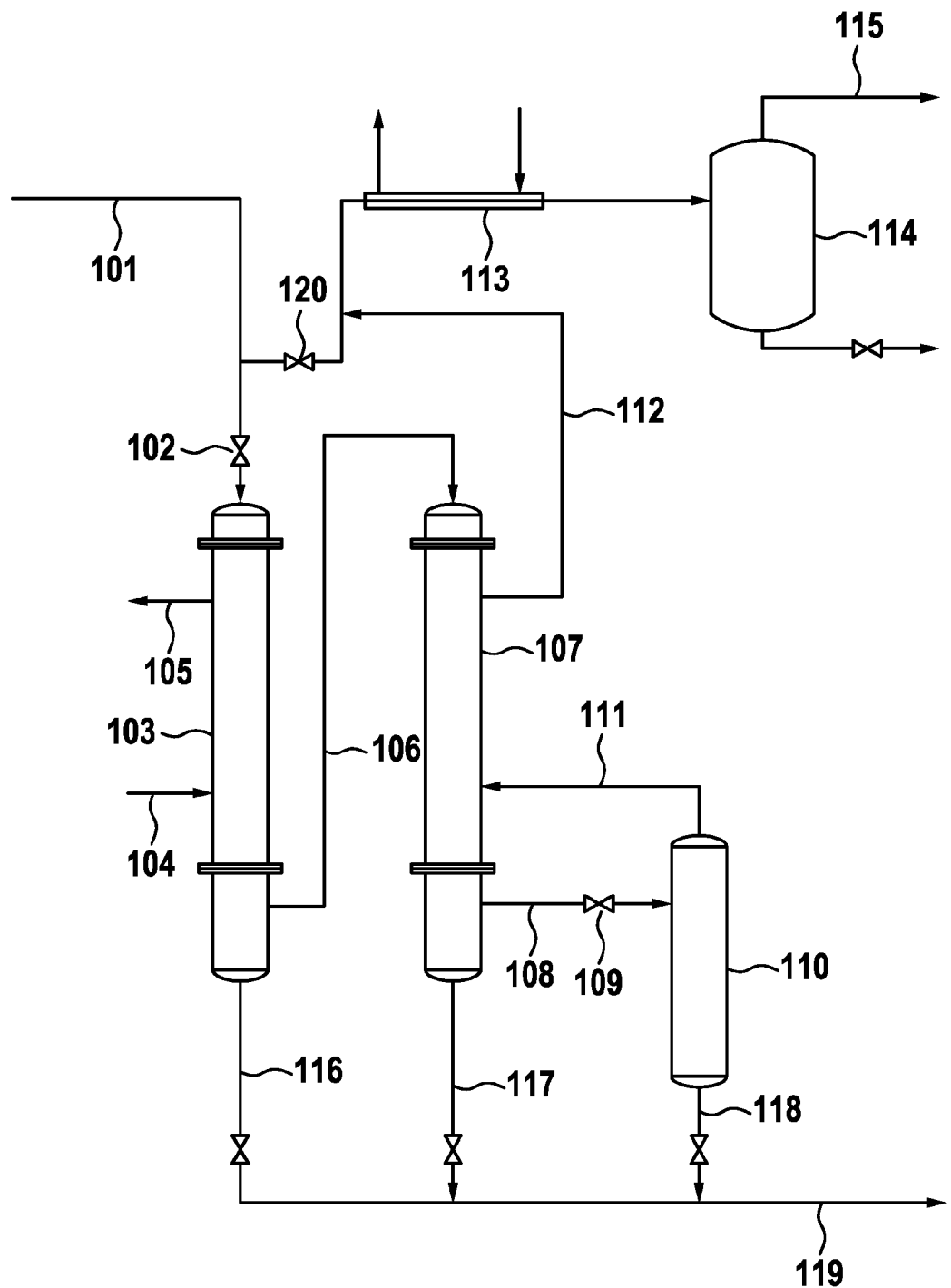
FIG. 2 shows schematically a set-up for a unit for separating ethylene and esters of vinyl alcohol such as vinyl acetate according to the process of the present invention.

FIG. 2 shows schematically a set-up for a unit for separating ethylene and esters of vinyl alcohol such as vinyl acetate according to the process of the present invention. Also FIG. 2 is described on the basis of vinyl acetate as ester of vinyl alcohol, this non-limiting the scope of the invention.

The gas stream comprising ethylene and vinyl acetate, for examples coming from a polymerization apparatus as shown in FIG. 1 via line (33) and having a pressure of 3.5 MPa, enters the separation unit via line (101). The gas mixture passes a regulation valve (102) and enters a first heat exchanger (103) in which it is cooled to a temperature of 5° C. by means of a water/glycol mixture as cooling medium, which enters the heat exchanger (103) via line (104) and exits via line (105). The not condensed part of the gas stream is transferred via line (106) to a second heat exchanger (107), in which it is cooled to a temperature of −10° C.

The not condensed part of the gas stream is then transferred via line (108) and pressure reduction valve (109) to a separation vessel (110). By passing valve (109) the pressure is reduced to 0.5 MPa. Caused by the pressure reduction, the temperature decreases. The not condensed part of the gas stream transferred to separation vessel (110) is withdrawn from separation vessel (110) as gas having a temperature of −40° C. and fed via line (111) as cooling medium to heat exchanger (107) for cooling the gas mixture entering the heat exchanger (107) via line (106). The slightly heated gas stream exits heat exchanger (107) via line (112), is further heated in heat exchanger (113), passes a separation vessel (114) and is the transferred via line (115) to an ethylene recovery unit or an ethylene producing or converting unit for further treatment.

The condensed parts of the gas stream, which mainly consist of vinyl acetate, are withdrawn from heat exchangers (103) and (107) and separation vessel (110) via lines (116), (117) and (118), combined and returned to the polymerization process via line (119). It is also possible first to purify the vinyl acetate and thereafter to return it to the polymerization process.

If, for example, the unit for separating ethylene and esters of vinyl alcohol shown in FIG. 2 is installed as part of a polymerization apparatus, valve (120) allows to by-pass the ethylene vinyl ester separation and transfer the gas stream coming via line (101) directly to an ethylene recovery unit via line (115), for instance if the polymerization is carried out without comonomer.

The invention claimed is:

1. A process for separating esters of vinyl alcohol from a gas stream comprising from 70 to 99.5% by weight of ethylene and from 0.5 to 30% by weight of esters of vinyl alcohol being at a pressure in the range of from 0.5 MPa to 10 MPa and a temperature in the range of from 5° C. to 50° C. comprising the steps of
 a) cooling the gas stream in a first heat exchanger by means of a cooling medium to a temperature of from −5° C. to 40° C.;
 b) withdrawing the not condensed part of the gas stream from the first heat exchanger and transferring it to a second heat exchanger;
 c) cooling the gas stream in the second heat exchanger to a temperature of from −20° C. to 5° C.;
 d) withdrawing the not condensed part of the gas stream from the second heat exchanger, reducing the pressure of the gas stream to from 0.2 MPa to 3 MPa and transferring it to a separation vessel;
 e) withdrawing the not condensed part of the gas stream from the separation vessel and transferring it as cooling medium to the second heat exchanger; and
 f) withdrawing the cooling medium as ethylene gas stream with a reduced content of esters of vinyl alcohol from the second heat exchanger.

2. A process according to claim 1, wherein, in a subsequently step g), the ethylene gas stream coming from the second heat exchanger is heated in a third heat exchanger to a temperature of from 10° C. to 50° C.

3. A process according to claim 1, wherein the pressure reduction of step d) decreases the temperature of the gas stream to from −70° C. to −10° C.

4. A process according to claim 1, wherein the content of esters of vinyl alcohol in the ethylene gas stream obtained in step f) is from 0.005 to 0.5% by weight.

5. A process according to claim 1, wherein vinyl acetate is separated from a stream comprising from 70 to 99.5% by weight of ethylene and from 0.5 to 30% by weight of vinyl acetate.

6. A process for copolymerizing ethylene and esters of vinyl alcohol in the presence of free-radical polymerization initiators at pressures in the range of from 110 MPa to 500 MPa and temperatures in the range of from 100° C. to 350° C. in a continuously operated polymerization apparatus comprising a process for separating esters of vinyl alcohol from a gas stream comprising from 70 to 99.5% by weight of ethylene and from 0.5 to 30% by weight of esters of vinyl alcohol according to claim 1.

7. A process for copolymerizing ethylene and esters of vinyl alcohol according to claim 6, wherein the gas stream comprising from 70 to 99.5% by weight of ethylene and from 0.5 to 30% by weight of esters of vinyl alcohol is off-gas from the continuously operated polymerization apparatus.

8. A process for copolymerizing ethylene and esters of vinyl alcohol according to claim 6, wherein the ethylene gas stream obtained in step f) is transferred to an ethylene recovery unit or to an ethylene producing or converting unit.

9. A process for copolymerizing ethylene and esters of vinyl alcohol according to claim 6, wherein the condensed parts of the gas stream obtained in steps a), c) and d) are returned to the polymerization process.

10. A process for copolymerizing ethylene and esters of vinyl alcohol according to claim 7, wherein the continuously operated polymerization apparatus comprises a polymerization reactor and at least one compressor, which compresses the monomer mixture, which is fed to the polymerization reactor, to the polymerization pressure, wherein non-reacted monomers of the polymerization process are fed to the compressor at a lower pressure than the fresh ethylene and wherein the monomer mixture is compressed by a sequence of compression stages in which the compressed gas mixture is cooled after each compression stage and the fraction of the monomer mixture, which is liquid after this cooling, is separated from the remaining gas and returned to the polymerization apparatus in liquid form, wherein the off-gas is taken from compressed monomer mixture after the last compression stage before the fresh ethylene is added and after the liquid fraction obtained in cooling this compressed monomer mixture is separated.

11. A process for copolymerizing ethylene and esters of vinyl alcohol according to claim 10, wherein at least a part of the liquid fractions obtained after compressing the monomer mixture in the respective compression stage to a pressure of from 0.2 MPa to 10 MPa is purified before being returned to the polymerization process.

12. A process for copolymerizing ethylene and esters of vinyl alcohol according to claim 10, wherein the polymerization reactor is a tubular reactor or an autoclave reactor.

* * * * *